United States Patent [19]

Mitchell et al.

[11] Patent Number: 5,096,698
[45] Date of Patent: Mar. 17, 1992

[54] PACKAGED DENTAL CREAM

[75] Inventors: Robert L. Mitchell, Cheshire, England; Gary A. Durga, Somerset, N.J.

[73] Assignee: Colgate-Palmolive Company, Piscataway, N.J.

[21] Appl. No.: 617,462

[22] Filed: Nov. 26, 1990

Related U.S. Application Data

[63] Continuation of Ser. No. 319,837, Mar. 3, 1989, abandoned, which is a continuation-in-part of Ser. No. 106,098, Oct. 8, 1987, abandoned.

[51] Int. Cl.$^5$ .............................................. A61K 7/16
[52] U.S. Cl. ........................................ 424/49; 424/57; 424/58; 222/92; 222/107
[58] Field of Search ............... 424/49, 57, 58; 222/92, 222/107

[56] References Cited

U.S. PATENT DOCUMENTS

| | | | |
|---|---|---|---|
| 3,691,272 | 9/1972 | Asche | 424/57 |
| 4,537,778 | 8/1985 | Clipper | 424/53 |

FOREIGN PATENT DOCUMENTS

| | | |
|---|---|---|
| 6075410 | 4/1985 | Japan . |
| 2100983 | 1/1983 | United Kingdom . |
| 2180155 | 3/1987 | United Kingdom . |

OTHER PUBLICATIONS

Thurow, Chem. Abst., 94, 414 (1981), Abst. #90319d.
Patent Abstracts of Japan, vol. 4, No. 38 (C-4) [520], Mar. 27, 1980, p. 163 C4 JP 55-13251-Raion Hamigaki, K. K. (Nagayuma).
Chemical Abstracts, vol. 93, No. 6, Aug. 11, 1980, p. 451, Abstract 53809x JP 80 13, 251-Lion Dentifrice (Nagayama).

*Primary Examiner*—F. T. Moezie
*Attorney, Agent, or Firm*—Paul Shapiro; Robert C. Sullivan

[57] ABSTRACT

Dental cream in contact with a polyolefin resin surface of a package such as a laminate tube, a mechanical dispenser or a flexible sachet. The dental cream contains a dentally acceptable water-insoluble alkaline earth metal salt, a liquid vehicle, a gelling agent and an additive which prevents syneresis. The liquid vehicle contains water, glycerine and sorbitol. The additive which prevents syneresis due to contact between the dental cream and the polyolefin resin is a nonionic block copolymer containing moieties of polyoxyethylene and polyoxypropylene.

18 Claims, No Drawings

PACKAGED DENTAL CREAM

CROSS-REFERENCE TO RELATED APPLICATIONS

This application is a continuation of application Ser. No. 07/319,837 filed Mar. 3, 1989, which is a continuation-in-part of 07/106,098, filed Oct. 8, 1987, both are now abandoned.

BACKGROUND OF THE INVENTION

Description of the Related Art

This invention relates to a dental cream packaged in a plastic laminate tube, mechanical dispenser, flexible sachet or the like. In particular, it relates to a dental cream in compatible contact with a polyolefin surface of a package such as a plastic laminate dental cream tube, mechanical dispenser or flexible sachet.

Dental creams have been packaged for many years in flexible metal tubes such as wax lined lead tubes, unlined aluminum tubes or aluminum tubes having an epoxy resin lacquer coating thereon. In recent years, flexible form-retaining laminated plastic tubes have been increasingly used.

Plastic laminated dental cream tubes typically comprise in inner polyolefin resin layer which is in direct contact with the dental cream and at least one intermediate layer, including an aluminum foil layer which inhibits loss of flavor from the dental cream. Desirably, an intermediate paper layer which provides stiffness to the tube is also present. The outer layers are typically of polyolefin resins, one of which may be colored white and bear printed indicia with a clear polyolefin laminate overlay to protect the indicia. Additional intermediate laminate layers of flexible plastic may also be present.

Mechanical dental cream dispensers may also have a polyolefin surface in contact with dental cream contained therein. In fact, the polyolefin itself may be the housing of the dispenser. Flexible sachet packets may also have a polyolefin surface in contact with dental cream.

Dental creams typically contain a liquid vehicle of water and humectant, a gelling agent solid vehicle and a water-insoluble dental polishing agent. A surface active is also generally included. Dental creams composed of such materials wherein the humectant comprises glycerine and sorbitol and the polishing material is an alkaline earth metal salt such as dicalcium phosphate have been successfully packaged in flexible metal toothpaste containers including aluminum tubes which are unlined or which have an internal coating of an epoxy resin lacquer layer. However, it is observed that when such dental creams are differently packaged in containers having an interior polyolefin surface such as plastic laminated dental cream tubes, mechanically operated dental cream dispensers or flexible sachets, that syneresis becomes a problem and liquids separate from solids, rendering the dental cream undesirable.

In earlier commonly assigned patent disclosures additives to prevent dental cream syneresis upon contact with a polyolefin surface have been disclosed for dental creams containing an alkaline earth metal phosphate or alpha-alumina trihydrate polishing agent. These disclosures are:

U.S. Pat. No. 4,702,905, granted Oct. 27, 1989, wherein the anti-syneresis additive for an alkaline earth phosphate dental cream is a polyethylene glycol;

U.S. Pat. No. 4,716,034, granted Dec. 29, 1989, wherein the anti-syneresis additive for an alpha-alumina trihydrate dental cream is a polyethylene glycol;

U.S. Pat. No. 4,728,508, granted Mar. 1, 1988, wherein the anti-syneresis additive for a dental cream in which the polishing agent is mainly an alkaline earth metal phosphate is propylene glycol;

U.S. Pat. No. 4,770,324, granted Sept. 13, 1988, as a continuation-in-part of, now abandoned, U.S. Ser. No. 808,756, filed Dec. 13, 1985, wherein the anti-syneresis additive for a dental cream in which the polishing agent is mainly an alkaline earth metal phosphate is an alkyl parahydroxybenzoate ester;

U.S. Pat. No. 4,716,836, granted Dec. 29, 187, wherein the anti-syneresis additive for an alpha-alumina trihydrate dental cream is a vegetable oil;

U.S. Pat. No. 4,705,680, granted Nov. 10, 1987, wherein the anti-syneresis additive for an alkaline earth metal phosphate dental cream is a vegetable oil; and U.S. Ser. No. 214,786, filed July 5, 1988, now abandoned, as a continuation of, U.S. Ser. No. 835,014, filed Feb. 28, 1986, wherein the anti-syneresis additive for a dental cream in which the polishing agent is mainly alpha-alumina trihydrate is benzoic acid.

In each of the foregoing patent disclosures condensates of ethylene oxide with propylene glycol, that is "Pluronic" materials, are generally disclosed as a type of surface-active material which may be present in the several dental creams containing the described particular anti-syneresis additives.

Japanese Public Disclosure No. 75410/85 to Ebine et al (Lion Corporation) describes a dentifrice in which glycerine is the sole humectant or mixed with another humectant, such as sorbitol, but which glycerine is, in any event, present in amount greater than 20% by weight of the dentifrice, since lesser amounts would result in undesirable evaporation of water when the dentifrice is packed in a container having a plastic container body, at least the barrel portion of which has a water permeability of at least $5g/m^2.day.50u$. The high glycerine dentifrice is formulated to avoid evaporation and weight loss in this particular type of container. The disclosure includes a general indication that polymer of ethylene oxide and propylene oxide may be employed as surface-active agent.

U.S. Pat. No. 4,556,553 to Suganuma et al (Lion Corporation) discloses dentifrices containing and aluminum oxide abrasive in a container having an oxygen permeability of at least $3cc/m^2.day.atm$ wherein antiseptic properties are improved by the presence of polyhydric alcohol, including mixture of sorbitol and glycerine. There is a general disclosure that condensates of ethylene oxide with propylene oxide may be used as a surface-active agent in the aluminum oxide dentifrices. Some dentifrice samples are described for comparative purposes which contain dicalcium phosphate with sodium lauryl sulfate as the sole surface active agent.

Japanese Public Disclosure 1321/80 published on Japanese Patent Application 86226/78 to Naganuma et al (Lion Dentifrice Company) discloses that liquid-solid separation in toothpaste containing an anionic surfactant and a polyoxyethylene block copolymer type surfactant (that is, a "Pluronic" surfactant) can be overcome by employing a binder or gelling agent of at least one of hydroxyethyl cellulose and/or xanthan gum rather than carrageenan, gum tragacanth, sodium carboxymethyl cellulose, poly(sodium acrylate) or guar gum. The toothpastes described contain a humectant such as glycerin, sorbitol, propylene glycol or polyethylene glycol. The only mixtures of humectants described in specific formulations including those which evince separation when a gelling agent other than hydroxyethyl cellulose or xanthan is employed, contain glycerine and propylene glycol.

U.S. Pat. No. 4,353,890 to Scott (Colgate-Palmolive Company) discloses toothpastes containing carrageenan gelling agent which is stabilized by microwave radiation to maintain viscosity. A dicalcium phosphate toothpaste containing such stabilized carrageenan with a mixed humectant of 4.5% by weight of glycerol and 17.5% by weight of sorbitol is exemplified and indicated to be subjected to storage tests, including when packaged in containers having body portions of polyethylene. The detergent or surface-active agent employed in the exemplified toothpaste is sodium lauryl sulfate. The patent includes a general disclosure "Pluronics (R)" as detergents.

It is an advantage of this invention that phase separation of a dental cream packaged in contact with a polyolefin material which would undergo phase separation but for the presence of an additive which overcomes syneresis, is substantially prevented. Other advantages will be apparent from consideration of the following disclosure.

SUMMARY OF THE INVENTION

In accordance with certain of its aspects, this invention relates to a packaged dental cream wherein said dental cream is in direct contact with a low or medium density polyethylene or polypropylene surface, wherein syneresis occurs in said dental cream due to said direct contact when said dental cream consists essentially of as ingredients about 20-75% by weight of a liquid vehicle consisting essentially of about 10-50% by weight of water, about 5.0-15% by weight of glycerine and about 10 to 35% sorbitol, the amount of glycerine and sorbitol together being about 15-50% by weight, the weight ratio of glycerine to sorbitol being from about 0.25:1 to about 1:1, about 0.05-10% by weight of a dental cream gelling agent selected from the group consisting of Irish Moss, gum tragacanth, sodium carboxymethyl cellulose, hydroxyethyl cellulose, polyvinyl pyrrolidone, sodium alginate, guar gum, starch, xanthan and iota-carrageenan, and about 20-65% by weight of a dentally acceptable water-insoluble calcium or magnesium alkaline earth metal salt polishing agent; said dental cream consisting essentially of said ingredients and as the sole additive to prevent syneresis in said dental cream upon said direct contact, about 0.1-5% by weight of a nonionic polyoxyethylene-polyoxypropylene block copolymer. The percentages by weight referred to above and throughout this specification mean weight percent of the dental cream, i.e. the entire dental cream.

DESCRIPTION OF THE PREFERRED EMBODIMENTS

In dental cream formulations, the liquids and solids are necessarily proportioned to form a creamy mass of desired consistency which is extrudible from its package. The liquids in the present dental cream comprise chiefly water, glycerine and sorbitol. The total liquid vehicle amounts to about 20-75% by weight of the formulation. A gelling agent in the dental creams is a natural or synthetic gum or gumlike material, particularly, e.g. Irish Moss (carrageenan), gum tragacanth, sodium carboxymethylcellulose, hydroxyethyl cellulose, polyvinyl pyrrolidone, sodium alginate, guar gum, starch, xanthan or iota-carrageenan, including mixtures thereof. Irish Moss, sodium carboxymethyl cellulose, and iota-carrageenan, including mixtures thereof are compatible particularly and are preferred gelling agents. The gum content is in a amount of about 0.05-10% and preferably about 0.5-5% by weight of the formulation.

Water is incorporated into the dental cream in amount of about 10-50% by weight, preferably about 15-35%. Glycerine and sorbitol together generally comprise about 15-50% by weight, preferably about 20-35% of the dental cream, with the amount of glycerine being about 5.0-15% by weight, the amount of sorbitol being about 10-35% by weight and the weight ratio of glycerine to sorbitol being from about 0.25:1 to about 1:1, typically from about 0.25:1 to about 0.8:1 and preferably from about 0.25:1 to about 0.6:1. It is preferred to use about 6-10% by weight of glycerine and about 17-24% by weight of sorbitol. Amounts of sorbitol as used herein are of sorbitol syrup, as commercially available, that is 70% by weight sorbitol in 30% by weight of water.

Dentally acceptable water-insoluble alkaline earth metal salt polishing agent is present in the dental cream in amount of about 20-75% by weight, preferably about 35-60%. Typical salts include dicalcium phosphate dihydrate, anhydrous dicalcium phosphate, calcium carbonate, tricalcium phosphate, calcium pyrophosphate, dimagnesium phosphate trihydrate and magnesium carbonate including mixtures thereof. Most preferably, calcium salt, particularly dicalcium phosphate dihydrate or mixture of dicalcium phosphate dihyrate and anhydrous dicalcium phosphate, is present.

In addition to the alkaline earth metal salt polishing agent, additional polishing agent such as hydrated alumina and calcined alumina may be present, for instance in a weight ratio of alkaline earth metal salt to alumina material of about 2.5:1 to about 4:1, the total amount of polishing material in the dental cream being about 25-75% by weight.

The single material employed in accordance with the present invention to prevent syneresis when the dental cream is in direct contact with a low or medium density polyethylene or polypropylene is a nonionic polyoxyethylene-polyoxypropylene block copolymer. The block copolymer is also effective in the dental cream as a surface-active agent. It is present in amount of about 0.1-5% by weight, preferably about 0.5-3%.

The nonionic surface-active agent employed in the instant invention is a block copolymer containing polyoxyethylene and polyoxypropylene. Such block copolymers are available from Wyandotte Chemicals Corporation under the trademark "Pluronic". They may be liquid, paste or solid and are generally chemically defined in terms of the molecular weight of the polyoxypropylene hydrophobic moiety and the percent by weight of the polyoxyethylene hydrophilic moiety. The following block copolymers are available from Wyandotte:

| Pluronic Number | Physical Character | Hydrophil | Mol. Wt. Hydrophobe |
|---|---|---|---|
| L121 | Liquid | 10 | 4000 |
| L101 | Liquid | 10 | 3250 |
| L81 | Liquid | 10 | 2250 |
| L61 | Liquid | 10 | 1750 |
| L31 | Liquid | 10 | 950 |

-continued

| Pluronic Number | Physical Character | Hydrophil | Mol. Wt. Hydrophobe |
|---|---|---|---|
| L122 | Liquid | 20 | 4000 |
| L92 | Liquid | 20 | 2750 |
| L72 | Liquid | 20 | 2050 |
| L52 | Liquid | 20 | 1750 |
| L42 | Liquid | 20 | 1200 |
| P123 | Paste | 30 | 4000 |
| P103 | Paste | 30 | 3250 |
| L63 | Liquid | 30 | 1750 |
| L43 | Liquid | 30 | 1200 |
| P104 | Paste | 40 | 3250 |
| P94 | Paste | 40 | 2750 |
| P84 | Paste | 40 | 2250 |
| P64 | Liquid | 40 | 1750 |
| P44 | Liquid | 40 | 1200 |
| P105 | Paste | 50 | 3250 |
| P85 | Paste | 50 | 2250 |
| P75 | Paste | 50 | 2050 |
| P65 | Paste | 50 | 1750 |
| P35 | Liquid | 50 | 950 |
| F127 | Solid | 70 | 4000 |
| F87 | Solid | 70 | 2250 |
| P77 | Solid | 70 | 2050 |
| F108 | Solid | 80 | 3250 |
| F98 | Solid | 80 | 2750 |
| F88 | Solid | 80 | 2250 |
| F68 | Solid | 80 | 1750 |
| F38 | Solid | 80 | 950 |

The preferred nonionic block copolymers are solid (or flake) materials and the most preferred are Pluronic F-108 (80% polyoxyethylene: 3250 molecular weight polyoxypropylene) and F-87 (70% polyoxyethylene: 2250 molecular weight polyoxypropylene), F-127 (70% polyoxyethylene: 4000 molecular weight polyoxypropylene) and L-72 (20% polyoxyethylene: 2050 molecular weight polyoxypropylene).

Since the nonionic block copolymer anti-syneresis agent does not provide substantial foam to the dental cream, an anionic surface-active agent may also be provided for its foaming character and in order to enhance detergency. The surface-active agents may achieve increased prophylactic action, assist in achieving thorough and complete dispersion of the instant compositions throughout the oral cavity and render the dental creams more cosmetically acceptable. Suitable anionic surface-active materials are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkylaryl sulfonates, such as sodium dodecyl benzene sulfonate, olefin sulfonates, such as sodium olefin sulfonate in which the olefin group contains 12-22 carbon atoms, higher alkyl sulfoacetates, higher fatty acid ester of 1,2-dihydroxy propane sulfonates, and the substantially saturated higher aliphatic acyl amides of lower aliphatic amino carboxylic acid compounds such as those having 12 to 16 carbon atoms in the fatty acid, alkyl or acyl radicals and the like. Examples of the last mentioned amides are N-lauroyl sarcosine, and the sodium, potassium, and ethanolamine salts of N-lauroyl, N-myristoyl or N-palmitoyl sarcosine, which should be substantially free from soap or similar higher fatty acid material which tends to substantially-reduce the effect of these compounds in compositions of the present invention. The amides are particularly advantageous since they exhibit a prolonged and marked effect in the inhibition of acid formulation in the oral cavity due to carbohydrate breakdown in addition to exerting some reduction in the solubility of tooth enamel in acid solutions. Another desirable material is a long chain fatty acid sodium monoglyceride sulfonate used alone or in combination with sodium lauryl sulfate. It is preferred to use about 0.2-5% by weight of total surface-active agent typically about 1-3%, when anionic surface-active agent is present.

The dental cream suitably may also contain a fluorine-containing compound having a beneficial effect on the care and hygiene of the oral cavity, e.g., diminution of enamel solubility in acid and protection of the teeth against decay. Examples thereof include sodium fluoride, stanous fluoride, potassium fluoride, potassium stannous fluoride ($SnF_2.KF$), sodium hexafluorostannate, stannous chlorofluoride, sodium fluorozirconate and sodium monofluorophosphate. These materials which disassociate or release fluorine-containing ions in water, suitably may be present in an effective but nontoxic amount, usually within the range of about 0.01 to 1% by weight of the water-soluble fluorine content thereof.

The preferred fluoride-containing compound is sodium monofluorophosphate, typically present in an amount of about 0.076 to 7.6% by weight, preferably 0.76%. A mixture of sodium monofluorophosphate and sodium fluoride is also desirable, for instance in a weight ratio of about 2:1 based on fluoride.

Any suitable flavoring or sweetening materials may be employed in formulating a flavor for the composition of the present invention. Examples of suitable flavoring constituents include the flavoring oils, e.g., oils of spearmint, peppermint, wintergreen, sassafras, clove, sage, eucalyptus, cinnamon, lemon and orange, as well as methyl salicylate. Suitable sweetening agents include sucrose, lactose, maltose, xylitol, sodium 6methyl-3, 4-dihydro-1,2,3-oxathiazine-4-one, sodium cyclamate, perillartine and sodium saccharin. Suitably, flavor and sweetening agents may together comprise from about 0.01 to 5% or more of the compositions of the instant invention.

Various other materials may be incorporated in the dental cream. Examples thereof are coloring or whitening agents or dyestuffs, preservatives such as sodium benzoate, anti-corrosive agents, silicones, chlorophylic compounds, ammoniated materials such as urea, diammonium phosphate and mixtures thereof and other constituents. Whitening agents, such as titanium dioxide, typically in amounts of about 0.5-2%, may be beneficial to the appearance of the dental composition, since upon aging, some discoloration may occur.

The adjuvants are incorporated in the instant composition in amounts which do not substantially adversely affect the properties and characteristics desired and are selected and used in proper amounts depending upon the particular type of composition involved.

Antibacterial agents may also be employed in the oral compositions of the instant invention in an amount of about 0.01-5% by weight. Typical antibacterial agents include:

$N^1$-(4chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-$N^5$-chlorobenzylbiguanide;
1,6-dichlorophenylbiguanidohexane;
1,6-bis-(2-ethylhexylbiguanido-hexane;
1-(lauryldimethylammonium)-8-(p-chlorobenzyldimethyl-ammonium) octane dichloride;

5,6-dichloro-2-guanidinobenzimidazole;
N¹-p-chlorophenyl-N⁵-laurylbiguanide;
5-amino-1,3-bis(2-ethylhexyl)-5-methylhexahydropyrimidine and their non-toxic acid addition salts.

There may be employed also various calcium and magnesium ion suppression agents for adjustment of physical properties of the compositions. Suitable agents are the water-soluble inorganic polyphosphate salts, such as tetrasodium pyrophosphate or disodium diacid pyrophosphate, with the partially neutralized or acid polyphosphate preferred. Other suitable agents are the alkali metal, preferably sodium, salts of citric acid. In general, such compounds will be a minor amount or proportion of the formulation. The precise amount will vary depending upon the specific formulation, such as the physical characteristics of the dental cream, but will usually be from about 0.1% to about 3% by weight.

The dental creams should have a pH practicable for use. A pH range of 5 to 10 is particularly desirable. The reference to the pH is meant to be the pH determination directly on the dental cream. If desired, materials such ascitric acid may be added to adjust to the pH to say 6 to 7.

The package into which the dental cream is incorporated may be any polyolefin laminate dental cream tube. For instance, the tube may be as elementary as is described in U.S. Pat. No. 3,260,410 to Brandt et al, the disclosure of which is incorporated herein by reference. As described in the example thereof, an aluminum foil base having a thickness of about 0.0013 cm was heated to a temperature of approximately 177° C., and one face of the heated foil was contacted by an extrudable film of a random copolymer of ethylene and acrylic acid (acid content 3±0.5% and melt index 8±1), while opposite surface thereof and replaced there against a film of low density polyethylene. Using driven rolls, a laminated base was obtained in which the copolymer layer was about 6 mils and the polyethylene layer was approximately 5 mils in thickness. The base was then shaped into tubular form and sealed.

After severing the tubular form into tube bodies, the tubes can be packed with the dental cream of the present invention without the dental cream undergoing syneresis.

Polyolefin laminate dentifrice tubes containing more intermediate layers may also be successfully used with the dental cream of the present invention without undergoing syneresis. For instance, the multiple layer flexible sheet structure for dental cream tubes described as "Prior Art" in U.S. Pat. No. 4,418,841 to Eckstein may be employed as well as the more crack resistant structures described therein. The disclosure of U.S. Pat. No. 4,418,841 to Eckstein is incorporated herein by reference. In fact, dental creams of the present invention packed in tubes of sheet material identified as Prior Art A and A-1 in U.S. Pat. No. 4,418,841 are very satisfactory and undergo substantially no syneresis. Such tubes A and A-1 are comprised of layers as set forth below, in the order of outermost layer to inner most layer.

| A | A-1 |
|---|---|
| 1.5 mil LDPE | 1.5 mil LDPE |
| 2.0 mil Pigmented LDPE | 2.0 mil Pigmented LDPE |
| 1.6 mil Paper | 1.6 mil Paper |
| 0.7 mil LDPE | 2.0 mil LDPE |
| 3.3 mil EAA | 1.0 mil OPP |
| 0.7 mil Foil | 1.0 mil EAA |

-continued

| A | A-1 |
|---|---|
| 2.0 mil EAA | 0.7 mil Foil |
| 1.2 mil LDPE | 2.0 mil EAA |
| 13.0 mil Total | 1.2 mil LDPE |
| | 13.0 mil Total |

In A and A-1 the abbreviations have the following meanings:
LDPE low density polyethylene
EAA ethylene acrylic acid
OPP oriented polypropylene Medium density polyethylene may replace low density polyethylene. In a dental cream sachet package medium density polyethylene is preferred.

Mechanically operated dispensers, such as the dispenser for, in particular, pasty substances, described in U.S. Pat. No. 4,437,591 to von Schuckmann, the disclosure of which is incorporated herein by reference, may also be used with the practice of the present invention. The housing of such dispensers is commonly composed of a polyolefin resin such as polypropylene. Thus the housing resin is in essence a layer, the inner surface of which is in contact with dental cream. When the dental cream of the present invention is packaged in such a polypropylene mechanical dispenser, it undergoes substantially no syneresis.

The following properties are typical of low and medium density polyethylene:

| Clarity | Low Density Polyethylene Transparent to Translucent | Medium Density Polyethylene Transparent to Translucent |
|---|---|---|
| Yield | 30,000 (1,085,000) | 29,500 Sq. in/lb./0.001-in 1,065,000 sq. cm/kg./ 0.001-cm) |
| Specific gravity | 0.910–0.925 | 0.926–0.940 |
| Tensile strength ASTM D-882 | 1,000–3,500 (6,900–24,150) | 2,000–5,000 lb./sq. in. 13,800–34,500 kPa.) |
| Elongation (percent) ASTM D-882 | 225–600 | 225–500 |
| Impact Strength (kg-cm) | 7–11 | 4–6 |
| Tear strength ASTM D-1922 | 100–400 (250–1,000 | 50–300 gm/0.001 in. Elmendorf 125–750 gm/0.001 cm. Elmendorf) |
| Heat seal range | 250–350 (120–175 | 260–310° F. 125–155° C.) |
| WVTR 90 percent RH ASTM E-96 | 1.2 (7.74 | 0.5–1.0 gm/24 hr/100 sq. in. @ 100° F. 3.23–6.45 gm/24 hr/100 sq. cm. @ 37° C.) |
| Gas transmission $O_2$-ASTM D-1434 | 250–840 | 165–335 cc/0.001-in./100 sq. in./24 hr. @ ATM 73° F. + 0% RH |
| | (150–515 | 100–205 cc/0.001 cm/100 sq. cm./24 hr. @ ATM 22.77° C. + 0% RH) |
| | 495–5,000 | 500–840 cc/0.001-in/100 sq. in./24 hr. @ ATM 73° + 0% RH |
| Gas transmission $CO_2$-ASTM D-1434 | (300–3,050 | 305–515 cc/0.001-cm/100 sq. cm/24 hr. @ ATM 22.77° C. + 0% RH) |
| Resistance to grease and oils | Varies | Good |
| Maximum Use Temperature (°C.) | 150 (65.5 | 180–220° F. 82–105° C.) |
| Minimum Use Temperature (°C.) | −60 (−51 | −60° F. −51° C.) |

| Clarity | Low Density Polyethylene Transparent to Translucent | Medium Density Polyethylene Transparent to Translucent |
|---|---|---|
| Dimension change at high RH (percent) | None | None |
| Machine performance | Fair | Fair |
| Printability | Good if treated | Good if treated |
| Heat shrinkable | Some types | Some types |

Typical of polypropylene grades which may be employed particularly as dispenser housing for the dental cream are those supplied by Shell Chemical Company as Polypropylene DP 5A03 and Polypropylene DP 5A03S. These controlled rheology products combine the processibility of 12 melt flow grades with higher practical impact strength (as measured by falling weight testing). They were designed for fast processing in multicavity molds.

Polypropylene grades DP 5A03 and DP 5A03S have the following typical properties:

| | Traditional Units | SI Units | ASTM Test |
|---|---|---|---|
| Melt flow | 12 g/10 min | 12 g/10 min | D 1238[1] |
| Density at 23° C. | 0.905 g/cc | 0.905 g/cc | D 1505 |
| Tensile yield strength, at 5.0 cm/min | 5000 psi | 34 MPa | D 638[2] |
| Yield elongation, at 5.0 cm/min | 9% | 9% | D 638[2] |
| 1% Secant modulus, at 0.5 cm/min | 190,000 psi | 1300 MPa | D 638[2] |
| Flexural modulus, at 0.13 cm/min, 5 cm span | 200,000 psi | 1375 MPA | D 790A[2] |
| Notched Izod impact strength, | | | |
| at 73° F./23° C. | 0.5 ft-lb/in | 26 J/m | D 256[2] |
| at 0° F./−18° C. | 0.3 ft-lb/in | 15 J/m | D 256[2] |
| Hardness, Rockwell | R92 | R92 | D 785 |
| Heat deflection temp., at 66 psi/455 kPA | 220° F. | 104° C. | D 648 |
| Vicat softening temp. | 305° F. | 152° C. | D 1525 |

[1]Condition 230/2.16
[2]ASTM Type 1 specimen, 0.32 cm thick (injection molded)

The advantages of the invention are also present when the dental cream is packed in a flexible sachet having an polyolefin surface, typically of low density or medium density polyethylene.

The following illustrative examples are further illustrative of the nature of the present invention but it is understood that the invention is not limited thereto. All amounts and proportions are by weight except as otherwise indicated.

EXAMPLE 1

The following dental creams are prepared to creamy consistencies and packed into tubes of each of laminated structures A and A-1, set forth above.

| | Parts | |
|---|---|---|
| | A | B |
| Glycerine (99.3%) | 10.00 | 10.00 |
| Sorbitol (70%) | 17.00 | 17.00 |
| Sodium Carboxymethylcellulose | 0.95 | 0.95 |
| Sodium Saccharin | 0.20 | 0.20 |
| Tetrasodium Pyrophosphate | 0.25 | 0.25 |
| Sodium Monofluorophosphate | 0.76 | 0.76 |
| Dicalcium Phosphate Dihydrate | 48.76 | 48.76 |
| Sodium Lauryl Sulfate | 1.10 | 1.10 |
| Flavor | 0.89 | 0.89 |
| Pluronic F-108 | 0.50 | — |
| Water | Q.S. to 100.00 | Q.S. to 100.00 |

Dental cream B begins to undergo syneresis and phase separation after aging for 8-10 days at room temperature. Dental cream A remains stable against such phase separation when aged at room temperature for periods exceeding one year.

EXAMPLE 2

Dental creams (A) and (B) are incorporated into a mechanical dispenser in accordance with U.S. Pat. No. 4,437,591 composed of polypropylene housing. Dental cream (A) retains its creamy consistency while dental cream B separates into liquid and solid phases. Similar results to those described in the above Examples are observed when:

(i) Each of Pluronic F-127 and F-87 replace Pluronic F-108;

(ii) Pluronic L-72 replaces Pluronic F-108;

(iii) Pluronic P-84 replaces Pluronic F-108;

(iv) the comparative amounts of glycerine and sorbitol (70%) are: 5:20 and 12:15;

(v) Each of Irish Moss and iota-carrageenan replace sodium carboxymethyl cellulose;

(vi) The dental creams are packed in laminated tubes in accordance with U.S. Pat. No. 3,260,410;

(vii) The dental creams are packed in crack-resistant laminated tubes in accordance with U.S. Pat. No. 4,418,841;

(viii) The dental creams are packed in flexible sachets of the following structure from outermost to innermost layer;

12.2 μ polyethylene terephthalate
21.3 μ white ethylene acrylic acid
9.0 μ foil
3.3 μ ethylene acrylic acid
25.4 μ medium density polyethylene; and (ix) Mixture of 0.3 parts of sodium carboxymethylcellulose and 0.6 parts of iota-carrageenan replace of sodium carboxymethyl cellulose as the sole gelling material.

It is understood that the foregoing detailed description is given merely by way of illustration and that variations may be made therein without departing from the spirit of the invention.

What is claimed is:

1. A packaged dental cream wherein said dental cream is in direct contact with a low or medium density polyethylene or polypropylene surface; said dental cream consisting essentially of:

a) as a foaming agent, an anionic surface active agent present in a quantity of about 0.2% to 5% by weight of said dental cream;

b) a mixed humectant system comprising glycerine, present in a quantity of about 5.0 to about 15%, by weight of said dental cream, and sorbitol, present in a quantity of about 10 to about 35% by weight of said dental cream;

c) water, present in a quantity of from about 10 to about 50% by weight of said dental cream; and d) a syneresis-inhibiting effective quantity of a nonionic polyoxyethylene-polyoxypropylene block copolymer, as the sole additive to inhibit syneresis.

2. The dental cream of claim 1 wherein said nonionic polyoxyethylene-polyoxypropylene block copolymer is present in a quantity of from about 0.1 to about 5% by weight of said dental cream.

3. The dental cream of claim 1 wherein the weight ratio of said glycerine to said sorbitol is from about 0.25:1 to bout 1:1.

4. The dental cream of claim 1 wherein said cream further comprises a dental gelling agent selected from the group consisting of Irish Moss, gum tragacanth, sodium carboxymethyl cellulose, hydroxyethyl cellulose, polyvinyl pyrrolidone, sodium alginate, guar gum, starch, xanthan, and iota carrageenan.

5. The dental cream of claim 4 wherein said gelling agent is present in a quantity of from about 0.05 to about 10% by weight of said dental cream.

6. The dental cream of claim 1 wherein said dental cream further comprises a dentally acceptable water insoluble calcium of magnesium alkaline earth metal salt polishing agent.

7. The dental cream of claim 6 wherein said polishing agent is present in a quantity of from about 20 to about 75% by weight of said dental cream.

8. A packaged dental cream wherein said dental cream is in direct contact with a low or medium density polyethylene or polypropylene surface; said dental cream consisting essentially of:

a) as a foaming agent, an anionic surface active agent present in a quantity of about 0.2 to 5% by weight of said dental cream;

b) a mixed humectant system comprising glycerine, present in a quantity of from about 5.0 to about 15% by weight of said dental cream, and sorbitol, present in a quantity of about from 10 to about 35% by weight of said dental cream;

c) water, in a quantity of about 10 to about 50% by weight of said dental cream;

d) a dental cream gelling agent selected from the group consisting of Irish Moss, gum tragacanth, sodium carboxymethyl cellulose, hydroxyethyl cellulose, polyvinyl pyrrolidone, sodium alginate, guar gym, starch, xanthan and iota carrageenan, said gelling agent being present in a quantity of about 0.05 to about 10% by weight of said dental cream;

e) a dentally acceptable, water insoluble calcium or magnesium alkaline earth metal salt polishing agent; and f) a nonionic polyoxyethylene polyoxypropylene block copolymer present in a quantity of from about 0.1 to about 5% by weight of said dental cream.

9. The packaged dental cream claimed in claim 8 wherein the weight ratio of glycerine to sorbitol is from about 0.25:1 to about 0.8:1.

10. The packaged dental cream claimed in claim 8 wherein said block copolymer is a solid material.

11. The packaged dental cream claimed in claim 8 wherein said solid block copolymer has about an 80% by weight hydrophilic polyoxyethylene content and a hydrophobic polyoxypropylene molecular weight of about 3250.

12. The packaged dental cream claimed in claim 8 wherein said gelling agent is sodium carboxymethyl cellulose, present in amount of about 0.5-5% by weight.

13. The packaged dental cream claimed in claim 8 wherein said water-insoluble alkaline earth metal salt is a calcium salt.

14. The dental cream claimed in claim 13 wherein said calcium salt is dicalcium phosphate dihydrate.

15. The packaged dental cream claimed in claim 8 wherein said dental cream is packaged in a plastic laminate tube the inner surface of which is low density.

16. The packaged dental cream claimed in claim 8 wherein said dental cream is packaged in a mechanical dispenser having a housing of polypropylene resin.

17. The packaged dental cream claimed in claim 8 wherein said dental cream is packaged in a flexible sachet, the inner surface of which is low density polyethylene or medium density polyethylene.

18. The packaged dental cream of claim 9 wherein about 6-10% by weight of glycerine and about 17-24% by weight of sorbitol are present and the weight ratio of glycerine to sorbitol is from about 0.25:1 to about 0.6:1.

* * * * *